United States Patent [19]
Madni et al.

[11] Patent Number: 6,007,482
[45] Date of Patent: Dec. 28, 1999

[54] ENDOSCOPE WITH STRETCHABLE FLEXIBLE SHEATH COVERING

[76] Inventors: Asad M. Madni, 3281 Woodbine St., Los Angeles, Calif. 90064; Lawrence A. Wan, 22350 Carbon Mesa Rd., Malibu, Calif. 90265; Robert K. Hansen, 3014 Wyoming, Burbank, Calif. 91505

[21] Appl. No.: 08/771,444

[22] Filed: Dec. 20, 1996

[51] Int. Cl.$^6$ ..................................................... A61B 1/04
[52] U.S. Cl. ..................... 600/115; 600/114; 600/116; 600/121
[58] Field of Search ................................ 600/114, 115, 600/116, 121, 122, 123, 124, 125, 144, 152, 146

[56] References Cited

U.S. PATENT DOCUMENTS

| | | | |
|---|---|---|---|
| 4,066,070 | 1/1978 | Utsugi | 600/114 |
| 4,176,662 | 12/1979 | Frazer | 600/116 X |
| 4,676,228 | 6/1987 | Krasner et al. | 600/115 |
| 4,690,131 | 9/1987 | Lyddy, Jr. et al. | 128/4 |
| 5,029,574 | 7/1991 | Shimamura et al. | 600/116 |

FOREIGN PATENT DOCUMENTS

| | | | |
|---|---|---|---|
| 36330-660 | 3/1988 | Germany | 600/115 |

OTHER PUBLICATIONS

Self–Propelling, Self–Locating Colonoscope; NASA Tech Briefs, Winter 1978.

*Primary Examiner*—Beverly M. Flanagan
*Attorney, Agent, or Firm*—Flehr Hohbach Test Albritton Herbert LLP

[57] ABSTRACT

An endoscope which is both flexible and easily cleaned having a pair of telescoping sections at its distal end one of which carries a camera and which are alternately actuated to provide movement through a body passageway by a Bowden type of cable. Such cable has an outer helical casing with an inner steel wire. Respectively attached to the two cylindrical sections are inflatable bladders which provide for the movement above which also are an integral part of the flexible sterilized sheath being held to the respective sections by O-rings.

5 Claims, 4 Drawing Sheets

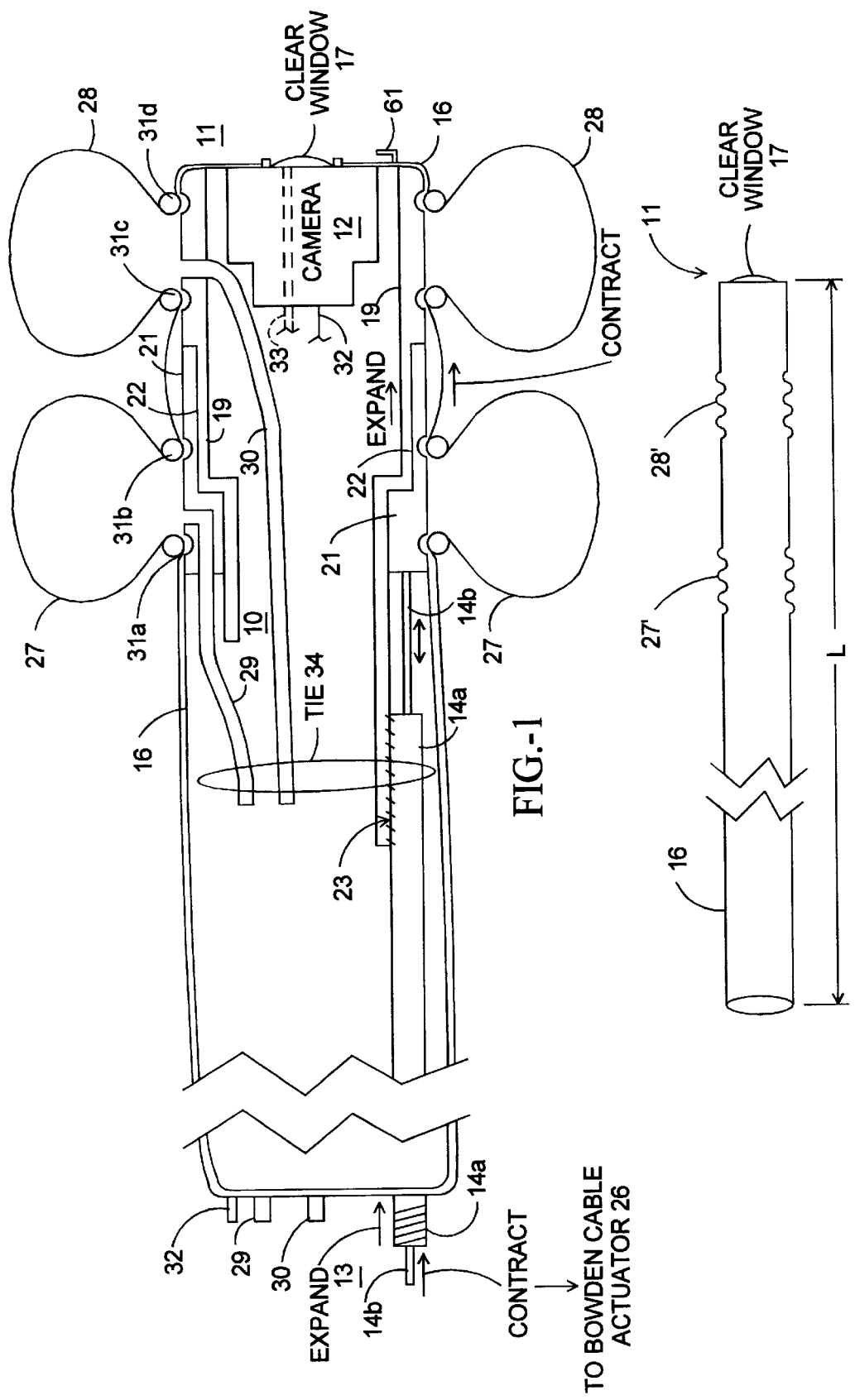

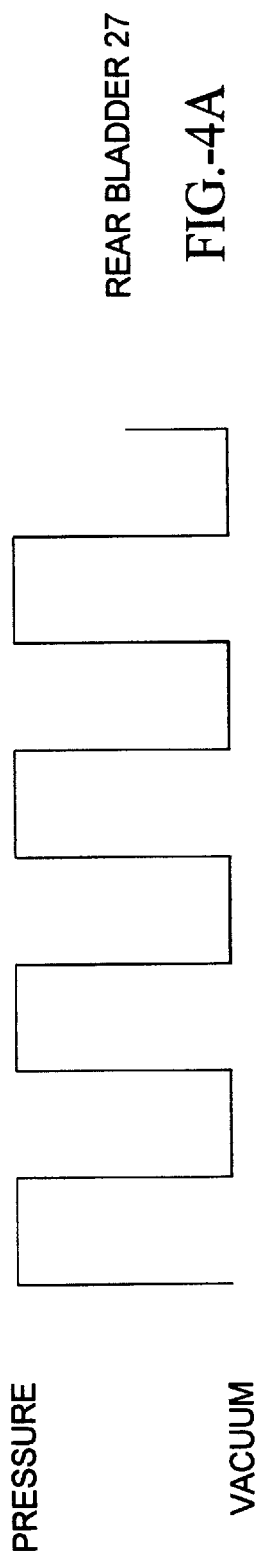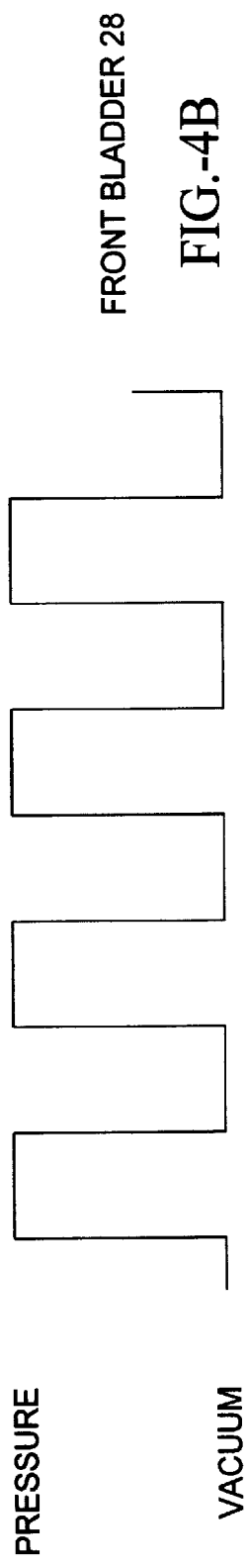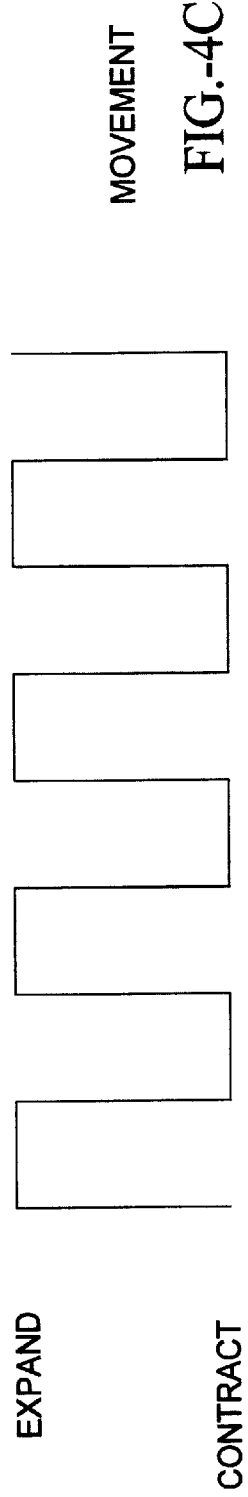

ENDOSCOPE WITH STRETCHABLE FLEXIBLE SHEATH COVERING

The present invention generally relates to an endoscope with stretchable flexible sheath covering and more specifically to an endoscope for use as a diagnostic tool in, for example, the colon.

BACKGROUND OF THE INVENTION

Endoscopes are well known and are in the form of a flexible tube for insertion into various body passageways such as the large and small intestines, and in addition, the stomach, etc. Since some body passageways, especially the colon, have many bend portions, the proper insertion of the endoscope can sometimes cause rupture or damage and, at least, excess pain. One difficulty is that the means for viewing the passageway in the gastrointestinal system includes a fiber optic device which necessarily requires a somewhat rigid conduit. To overcome the disadvantages of this rigidity it has been suggested, as for example by the Frazer U.S. Pat. No. 4,176,662 to utilize a self-propulsion system by two radially expandable bladders. Another bladder type system is suggested by Krasner U.S. Pat. No. 4,676,228. Both of these systems insufficiently deal with problems of flexibility and more importantly, for medical purposes, cleaning after use.

OBJECTS AND SUMMARY OF THE INVENTION

It is therefore an object of the present invention to provide an improved endoscope which is flexible and has greater ease of cleaning.

In accordance with the above object there is provided an endoscope with means for viewing a passageway of a human patient having a distal viewing end and an opposite proximal end. It comprises an elongated flexible assembly having proximal and distal ends and at its distal end carrying the viewing means and movable through the passageway by a pair of alternately inflatable bladders which cause movement by a caterpillar type action. A unitary impermeable and strechable flexible sheath covers the elongated assembly and forms the alternately inflatable bladders. The sheath has an integral window means at the distal end for enabling said viewing means.

BRIEF DESCRIPTION OF DRAWINGS

FIG. 1 is a simplified cross sectional view of an endoscope embodying the present invention.

FIG. 2 is a cross sectional side view of the flexible sheath of the endoscope of FIG. 1.

FIGS. 4A, 4B, and 4C are timing diagrams explaining the operation of FIG. 3.

DETAILED DESCRIPTION OF PREFERRED EMBODIMENTS

Figure 3:
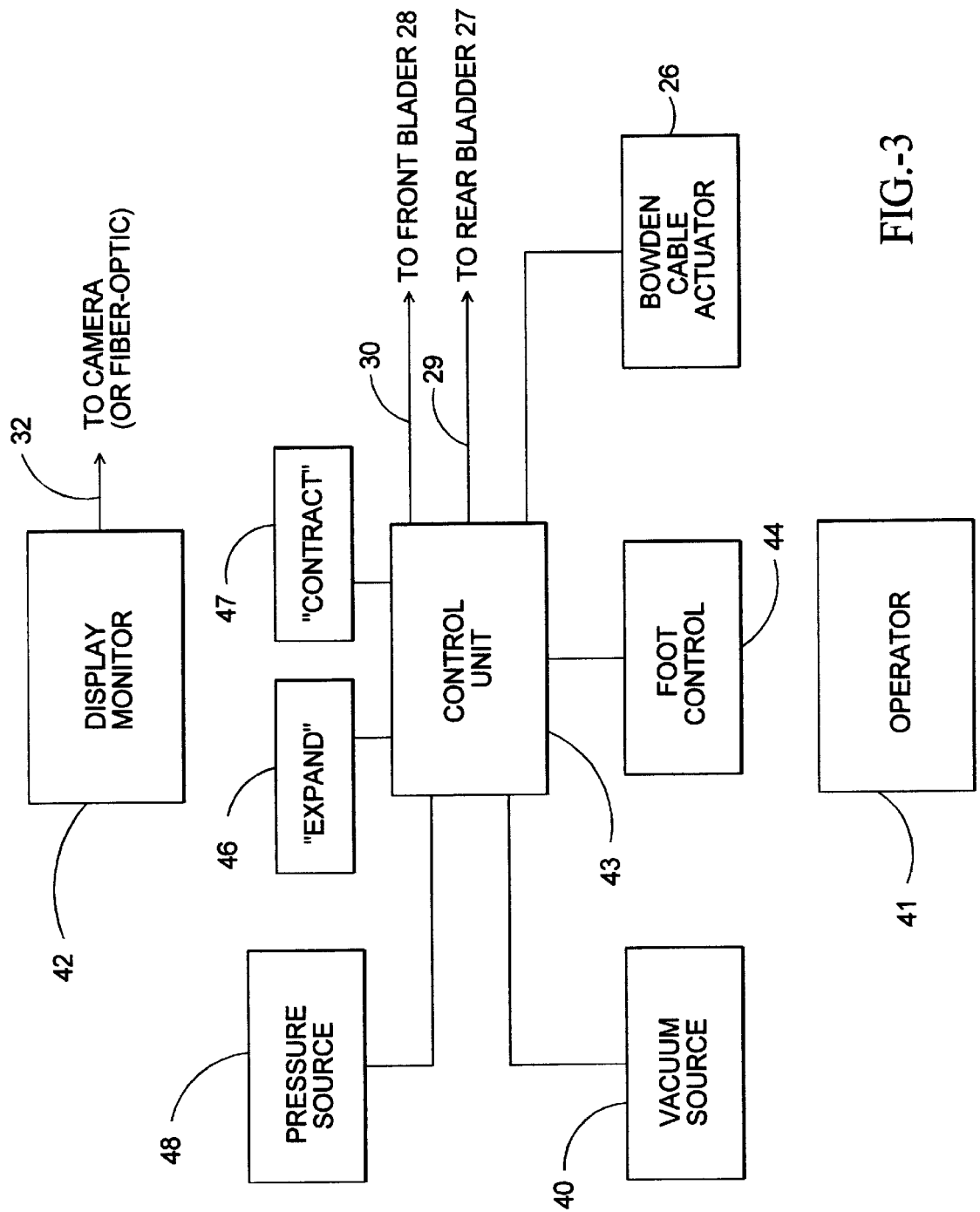
FIG. 3 is a block diagram showing the operation of the present invention.

FIG. 1 illustrates at 10 an elongated flexible assembly which carries at its distal end 11 a camera 12 and at its proximal end 13, the actuating end, a coaxial cable with a helically wound casing 14a with a spring steel wire 14b movable therein. This may be what is termed a Bowden type cable which is used in endoscopes for the purpose of steering.

To complete the endoscope of the present invention and also referring to FIG. 2 a unitary relatively impermeable and stretchable flexible sheath 16 is stretched over and covers the entire length, L, of the elongated flexible assembly 10. The sheath may be constructed of, for example, latex or other suitable stretchable flexible material. At its distal end 11 the sheath includes as an integral part a clear viewing window 17 which is placed opposite the lens of camera 12 to enable the viewing capability of the camera when in the passageway of a human patient. Sheath 16 is useable once and then a new sheath may be utilized which is sterilized. Since it is impermeable it protects against any possible contamination by the elongated flexible assembly 10.

Referring now in more detail to the elongated flexible assembly 10 in FIG. 1 it includes a pair of relatively rigid cylindrical sections 19 and 21 (metal or plastic) which are slidable within one another as shown by the step portion 22. Telescopic portion or section 19 carries camera 12 and it is also a part of or connected to as shown at 23 of the outer casing 14a of the coaxial actuating cable. Telescopic portion or section 21 on the other hand is connected to the inner wire 14b. Thus actuation of the cable 14a, 14b by a Bowden cable actuator 26 (see FIG. 3) which may be merely a rotary device, of telescoping sections 19 and 21 provides a worm-like or caterpillar type action to advance the endoscope in the body passageway.

Sheath 16 besides its sterile function also integrally forms a pair of alternately and selectively inflatable ring-type bladders 27 and 28. To create the inflatable bladders 27 and 28 the sheath, as illustrated in FIG. 2, when uninflated may include more relaxed corrugated portions shown illustrated as 27', 28'. Because of the stretchability of at least that portion of the bladder they are selectively inflated by air pressure tubes 29 and 30. The inflatable bladders 27 and 28 (which are normally not both inflated at the same time except for a brief moment) are held respectively to sections 21 and 19 by O-rings 31a through 31d. Since the bladders are an integral or a part of unitary sheath 16, a sterile environment is maintained. Yet easy removal and replacement is possible because of the O-rings.

Camera 12 has a wire 32 extending from it on which the pictorial information may be transmitted. Alternatively a fiber optic viewing bundle 33 may be used instead of a camera but this must be very flexible.

Thus, in summary, the elongated flexible assembly 10 includes a tie unit 34 which forms a relatively flexible tail which includes the Bowden type cable 14a, 14b, the pressure tubes 29 and 30 and either a electrical data wire 32 or a very thin fiber optic bundle 33. And over this, of course, is the sheath 16. This constitutes, especially with the use of a camera, a very flexible endoscope which by use of the alternately inflatable bladders 27 and 28 may be easily maneuvered through curves, for example, in the small intestine.

A medical specialist would, of course, operate this device as illustrated in FIG. 3. This person is designated as operator 41. The camera output is shown on the display monitor 42 which is tied to the camera by the line 32. An overall control unit 43 may include microprocessor capability or digital circuitry. When the control unit actuates the Bowden cable actuator 26 by, for example, the use of a foot control 44 by the operator, the operator might look at the control indicators "expands" 46 and "contract" 47 to determine movement if a movement is suitable. As will be explained in detail below, "expand" pushes the endoscope forward in the body passageway and "contract" is the movement where the telescoping sections are again brought together. This is shown by the labeled arrows in FIG. 1. Control unit 43 has a pressure source 48 and a vacuum source 49 which are selectively connected to the front bladder 28 and rear bladder 27 by tubes 30 and 29.

Figure 5A:
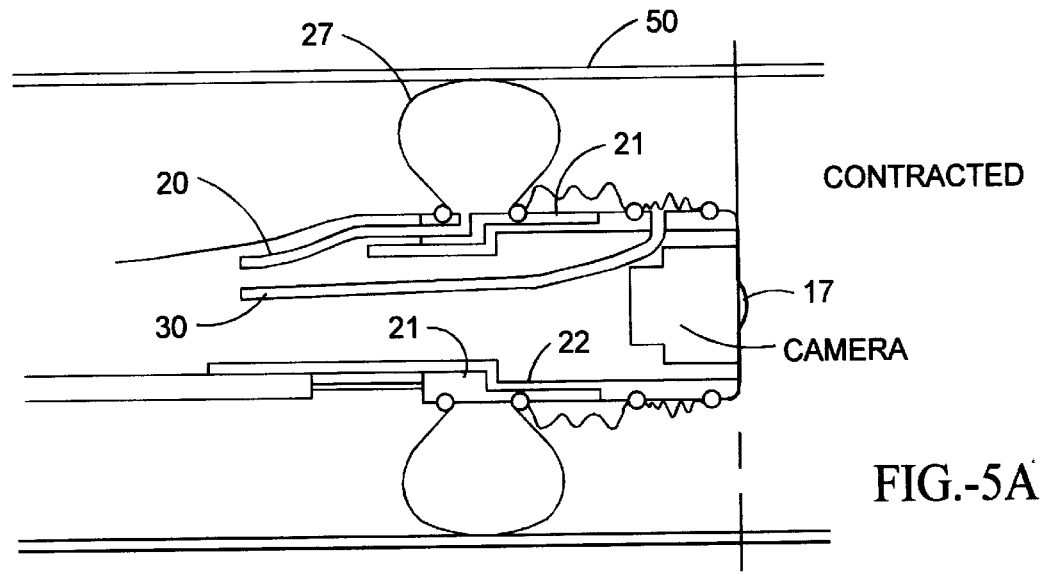
FIGS. 5A, 5B and 5C are cross sectional views similar to FIG. 1. showing the operation of the invention.
Figure 5B:
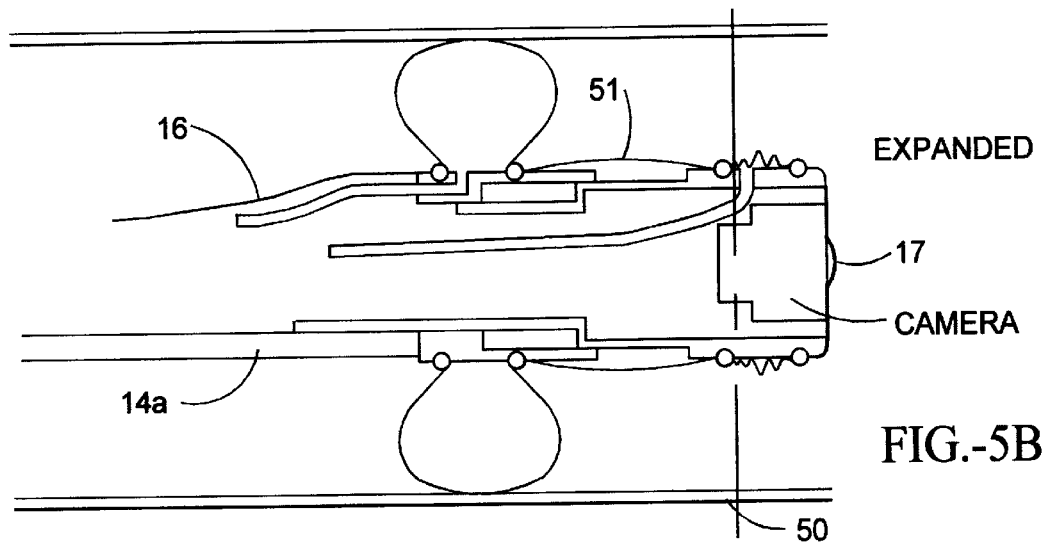
Figure 5C:
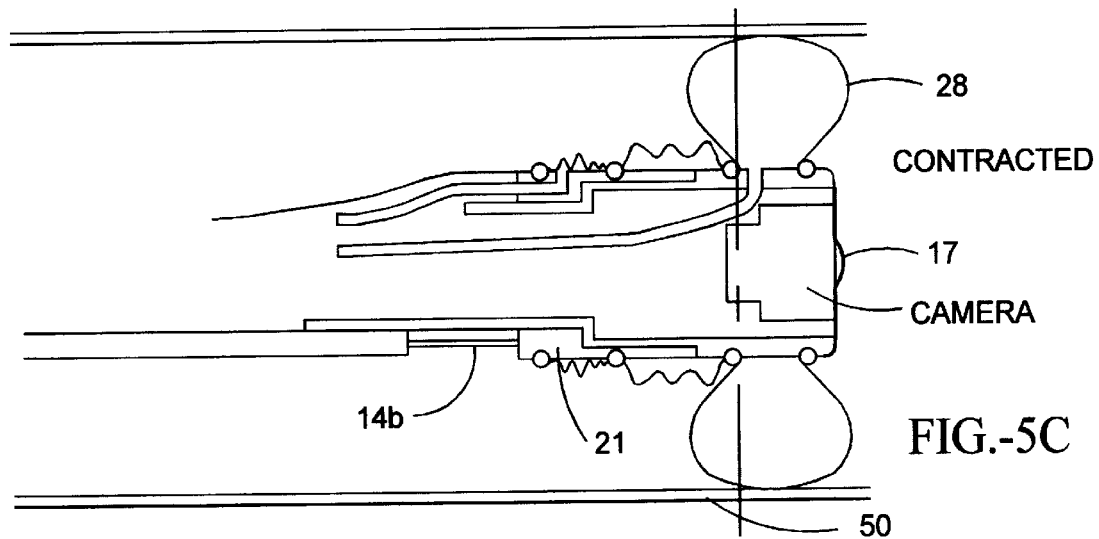

FIGS. 5A, 5B and 5C show the sequence of operation where in FIG. 5A the telescoping cylindrical sections 21 and 22 are together in a connected state and the rear bladder 27 is inflated anchoring the section 21 in the passageway designated 50.

Then actuation of the foot control 44 causes an expansion as illustrated in FIG. 5B by movement of the outer casing of the Bowden cable 14a forward along with section 19. This movement is accommodated by the flexible sheath 16 at 51 because of its flexibilty. And the camera and window 17 move forward as illustrated in FIG. 5B stretch ability further into the passageway 50.

Finally the next stepwise, worm-like or caterpillar type movement is provided by a contraction mode illustrated in FIG. 5C where with the front bladder 28 expanded in passageway 50 the telescoping section 21 is moved back into contact by the movement of the inner wire 14b. This process can also be reversed to cause the endoscope to move backwards. Of course, the rear bladder has been deflated by use of the vacuum source 49.

FIGS. 4A, 4B and 4C illustrate the foregoing movement. When the rear bladder 27, in FIG. 4A, has pressure applied to it, then as illustrated in FIG. 4C, expansion occurs. And then contraction mainly occurs with the front bladder inflated (FIG. 4B). There is some overlap.

By use of the telescoping sections which have a very minor length dimension compared to the entire endoscope, tight curves in a body passageway can be easily maneuvered around. Moreover this type of movement is made possible from a practical standpoint by the use of a flexible stretchable relatively impermeable latex sheath 16 which protects the entire flexible assembly and because it also forms the inflatable bladders, provides a simple and easy technique of cleaning; that is, after one use, it can simply be removed and replaced with a new sterile sheath. This is especially important with an endoscope since a camera or fiber optic cable cannot be autoclaved.

Miniature cameras (e.g., CCD cameras) would be suitable. If desired and from a practical standpoint, various suction and washing tubes can also be made a part of the construction illustrated at 61 in FIG. 1.

Thus an improved flexible and surgically sterile endoscope has been provided.

What is claimed is:

1. An endoscope for viewing a passageway of a human patient comprising:

an elongated flexible assembly having proximal and distal ends, including elongated coaxial cable driving means for moving said endoscope through a passageway of a human patient, said coaxial cable means having first and second moving components actuated from said proximal end of said flexible assembly;

said flexible assembly also including at said distal end a pair of relatively rigid cylindrical sections slidable and telescoping within one another, one of said sections carrying means for viewing said passageway and connected to one of said cable components, the other section being connected to said other cable component, actuation of said cable means causing said telescoping of said coaxial sections;

a unitary relatively impermeable stretchable flexible sheath covering said elongated assembly throughout its length and having an integral window means at its distal end for enabling said viewing means, and near its distal end including a pair o inflatable ring type bladders respectively connected to said pair of cylindrical sections and movable therewith and when inflated anchoring a selected section in said passageway;

said flexible assembly including air tube means for selectively inflating said bladders.

2. An endoscope as in claim 1 where said flexible sheath is useable once and is easily removable from said flexible assembly.

3. An endoscope as in claim 1 where said inflatable ring type bladders are connected to said cylindrical sections by O-rings.

4. An endoscope for viewing a passageway of a human patient comprising:

an elongated flexible assembly having proximal and distal ends and at its distal end carrying means for viewing a passageway of a human patient and movable through said passageway by a pair of alternately inflatable bladders which cause such movement by a caterpillar type action;

a unitary relatively impermeable and stretchable flexible sheath covering said elongated assembly and forming said alternately inflatable bladders and having an integral window means at its distal end for enabling said viewing means.

5. An endoscope as in claim 2 where said sheath is latex rubber.

* * * * *